United States Patent [19]

Gurgiolo

[11] 4,268,683

[45] May 19, 1981

[54] PREPARATION OF CARBAMATES FROM AROMATIC AMINES AND ORGANIC CARBONATES

[75] Inventor: Arthur E. Gurgiolo, Lake Jackson, Tex.

[73] Assignee: The Dow Chemical Company, Midland, Mich.

[21] Appl. No.: 123,137

[22] Filed: Feb. 21, 1980

[51] Int. Cl.³ .............. C07C 125/065; C07C 125/067; C07C 125/073; C07C 125/075
[52] U.S. Cl. ........................................ 560/24; 560/25; 560/26; 560/27; 560/28; 560/29; 560/32; 252/431 C
[58] Field of Search ...................... 560/24, 25, 26, 27, 560/28, 29, 32

[56] References Cited

U.S. PATENT DOCUMENTS

| | | | |
|---|---|---|---|
| 3,763,217 | 10/1973 | Brill | 560/24 |
| 3,895,054 | 7/1975 | Zajacek et al. | 560/24 |
| 3,919,279 | 11/1975 | Rosenthal et al. | 260/453 P |
| 3,919,280 | 11/1975 | Rosenthal et al. | 260/453 P |
| 3,962,302 | 6/1976 | Rosenthal et al. | 260/453 P |

OTHER PUBLICATIONS

Mukai et al., Chem. Absts., 87, 52961(e), 1977.
Olah, Friedel–Crafts and Related Reactions, vol. 1, Interscience Publishers, pp. 288–291 (1963).

Primary Examiner—Natalie Trousof
Assistant Examiner—G. T. Breitenstein
Attorney, Agent, or Firm—J. G. Carter

[57] ABSTRACT

Carbamates are prepared from organic cabonates and aromatic amines in the presence of zinc or tin salts of monovalent organic compounds having a pKa value of at least 2.8 such as zinc naphthenate and which are soluble at the reaction conditions.

8 Claims, No Drawings

PREPARATION OF CARBAMATES FROM AROMATIC AMINES AND ORGANIC CARBONATES

BACKGROUND OF THE INVENTION

Lewis acids have been disclosed in U.S. Pat. No. 3,763,217 as being suitable catalysts for reacting an organic carbonate with an aromatic amine to prepare carbamates.

It has been unexpectedly discovered that zinc and divalent tin salts provide the desired carbamates in higher yields and/or selectivity than the particular Lewis acids disclosed by Brill in U.S. Pat. No. 3,763,217.

SUMMARY OF THE INVENTION

The present invention pertains to an improvement in a process for preparing a carbamate from an organic carbonate and an aromatic amine in the presence of a catalytic quantity of a Lewis acid under suitable reaction conditions to produce said carbamate wherein the improvement comprises employing as the Lewis acid a zinc or divalent tin halide or a zinc or divalent tin salt of a monovalent organic compound having a pKa value of at least about 2.8, preferably from about 4 to about 10 and is soluble in the reaction mixture at the reaction conditions.

DETAILED DESCRIPTION OF THE PREFERRED EMBODIMENTS

Suitable organic carbonates which can be employed in the process of the present invention include the alkyl, aryl or alkyl aryl esters of carbonic acid. The ester group can be an alkyl group having up to about 12 carbon atoms, preferably a lower alkyl group containing up to about 6 carbon atoms or the ester group can be an aryl group containing up to about 10 carbon atoms.

Particularly suitable organic carbonates are the cyclic and acyclic organic carbonates such as for example ethylene carbonate, propylene carbonate, styrene carbonate, dimethyl carbonate, diethyl carbonate, dipropyl carbonate, dibutyl carbonate, dihexyl carbonate, methyl ethyl carbonate, methyl butyl carbonate, diphenyl carbonate, methyl phenyl carbonate, mixtures thereof and the like.

Any aromatic amine having a conjugate pKa value of from about 3.5 to about 5.5 is suitable for use herein with those amines having a conjugate pKa value of from about 4 to about 5.4 being preferred.

Suitable such aromatic amines include those represented by the formulas

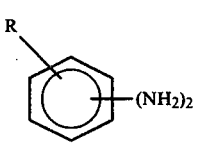

-continued

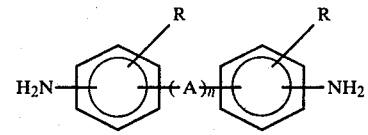

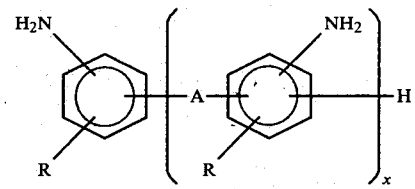

wherein each R is independently hydrogen or a hydrocarbyl or hydrocarbyloxy group containing up to about 8 carbon atoms, preferably up to about 4 carbon atoms, A is a divalent hydrocarbon group having from 1 to about 10 carbon atoms, preferably from 1 to about 6 carbon atoms, n has a value of zero or 1 and x has an average value of from about 1.1 to about 10, preferably from about 2 to about 4.

Particularly suitable amines include, for example, aniline, o-, m- or p-toluidine, 2,4-xylidine, 3,4-xylidine, 2,5-xylidine, 4-ethylaniline, 3-propylaniline, 1,3-diaminobenzene, 2,4-diaminotoluene, 2,6-diaminotoluene, 4,4'-diamino-diphenyl methane, 2,4,4'-triamino-diphenyl ether, 2,6-diamino naphthalene, 4,4'-bis-methylene diphenylamine, o-, m- or p-anisidine mixtures thereof and the like.

Suitable catalysts which can be employed herein include zinc or divalent tin salts of monovalent organic compounds having a pKa value above about 2.8, preferably from about 4 to about 10 and are soluble in the reaction mixture at the reaction conditions.

Suitable such catalysts include, for example, zinc acetate, zinc propionate, zinc octoate, zinc naphthenate, zinc benzoate, zinc pivalate, zinc stearate, zinc itaconate, zinc p-chlorobenzoate, zinc methoxide, zinc phenolate, zinc acetylacetonate, zinc chloride, stannous chloride, stannous octoate, mixtures thereof and the like.

When the organic carbonate is a cyclic organic carbonate, such as, for example, ethylene carbonate, a zinc or divalent tin salt of trifluoroacetic acid can be employed, even though trifluoroacetic acid has a pKa value below about 2.8.

The reaction is generally conducted at a temperature of from about 80° C. to about 300° C., preferably from about 120° C. to about 250° C. and most preferably from about 130° C. to about 200° C. for a time sufficient to complete the reaction depending upon the particular catalyst, reactants and temperature employed. Usually around 150° C., the time is from about one hour to about six hours, preferably from about two hours to about four hours. The reaction generally should be conducted under conditions at which none of the reactants or desired product undergo decomposition.

The quantity of catalyst employed usually depends upon the activity of the particular catalyst. Usually from about 0.001 mole to about 0.2 mole, preferably from about 0.005 mole to about 0.05 mole of catalyst per mole of reactant present in a stoichiometric quantity is suitable.

The reactants can be employed on an equimolar basis or one may be present in an excess of the other up to about a 20, preferably from about one to about five moles in excess of the other. It is preferred that the organic carbonate reactant be employed in excess of the aromatic amine.

Uses for the desired carbamate reaction product is suitably discussed by Rosenthal et al in U.S. Pat. Nos. 3,919,279, 3,919,280 and 3,962,302, all of which are incorporated herein by reference.

The following examples are illustrative of the present invention but are not to be construed as to limiting the scope thereof in any manner.

EXAMPLES 1–73 AND COMPARATIVE EXPERIMENTS A–P

In the following examples and comparative experiments, aniline and dimethyl carbonate were premixed employing an excess of the carbonate and a quantity of the mixture was then mixed with catalyst and poured into a stainless steel cylindrical container, 1⅝" internal diameter, and 2¼" internal depth with a wall thickness of 3/16". A stainless steel lid screwed over the reactor with a polytetrafluoroethylene O-ring being used as a seal. Mounted on the lid using stainless steel pipe fittings and parts were a pressure gauge, a pressure relief valve, and a needle valve.

After charging the mixture to the reactor, the lid was sealed by tightening down on the polytetrafluoroethylene O-ring and the reactor was immersed in a hot fluidized sand bath thermostatically controlled at 140° C. in the center of the bath. The reactor was heated 10 to 15 minutes then shaken to mix the contents. Then heating was continued for the desired time. After cooling the contents were analyzed for yields of carbamate and by-products.

The quantity of reactants, catalysts, reaction conditions and results are given in the following Table I.

TABLE I

| EXAMPLE OR EXPT. NO. | CATALYST TYPE | CATALYST g/mole | pKa[12] OF ORGANIC COMPOUND | ANILINE g/mole | DIMETHYL CARBONATE g/mole | REACTION TIME Hrs. | REACTION TEMP. °C. | CONDITIONS PRESS.[14] psi(kg/cm²) | MPC[1] g/mole | REACTION PRODUCTS NMA[2] g/mole | DPU[3] g/mole | WEIGHT RATIO MPC/NMA | % CONVERSION OF ANILINE TO MPC[10] |
|---|---|---|---|---|---|---|---|---|---|---|---|---|---|
| 1 | zinc acetate | 0.46 /0.0025 | 4.74 | 18.6/0.2 | 27.2/0.3 | 2 | 140 | 200 (14) | 14.94/0.0988 | 1.02 /0.0095 | 1.3 /0.0064 | 14.65/1 | 49.4 |
| 2 | zinc acetate | 0.46 /0.0025 | 4.74 | 18.6/0.2 | 27.2/0.3 | 8 | 140 | 210 (15) | 18.28/0.1209 | 1.62 /0.0151 | 1.21 /0.0060 | 11.28/1 | 60.45 |
| 3 | zinc acetate | 0.46 /0.0025 | 4.74 | 18.6/0.2 | 27.2/0.3 | 13 | 140 | 220 (15) | 22.55/0.1492 | 2.03 /0.0189 | 1 /0.0049 | 11.11/1 | 74.6 |
| 4 | zinc acetate | 0.46 /0.0025 | 4.74 | 18.6/0.2 | 27.2/0.3 | 22 | 140 | 170 (12) | 23.32/0.1543 | 1.85 /0.0173 | 0.72 /0.0036 | 12.61/1 | 77.15 |
| 5 | zinc naphthenate[4] | 0.41 /0.0005 | U.A.[11] | 5 /0.0537 | 25 /0.2775 | 1 | 140 | 170 (12) | 2.7 /0.0179 | 0.2 /0.0019 | 0.2 /0.0010 | 13.5 /1 | 33.3 |
| A | uranium trioxide | 0.143 /0.0005 | N.A.[13] | 5 /0.0537 | 25 /0.2775 | 2 | 140 | 130 (9) | 0.12 /0.0008 | 0.55 /0.0051 | 0.02 /0.0001 | 0.22/1 | 1.49 |
| B | uranium trioxide | 0.143 /0.0005 | N.A. | 5 /0.0537 | 25 /0.2775 | 5 | 140 | 150 (11) | 0.3 /0.002 | 0.93/0.0087 | 0.17 /0.0008 | 0.32/1 | 3.72 |
| 6 | zinc naphthenate[4] | 2.043 /0.0025 | U.A. | 5 /0.0537 | 25 /0.2775 | 2 | 140 | 110 (8) | 7.5 /0.0496 | 0.1 /0.0009 | 0.44 /0.0022 | 75 /1 | 92.36 |
| C | uranium trioxide | 0.715 /0.0025 | N.A. | 5 /0.0537 | 25 /0.2775 | 2 | 140 | 150 (11) | 0.07/0.0005 | 0.2 /0.0019 | 0 /0 | 0.35/1 | 0.93 |
| D | uranium dioxide | 0.4 /0.0015 | N.A. | 5 /0.0537 | 25 /0.2775 | 2 | 140 | 150 (11) | 0.16/0.0011 | 0.35 /0.0033 | 0.13 /0.006 | 0.46/1 | 2.05 |
| 7 | zinc naphthenate[5] | 0.327 /0.0005 | U.A. | 5 /0.0537 | 25 /0.2775 | 1 | 140 | 160 (11) | 2.32/0.0153 | 0.17 /0.0016 | 0.26 /0.0013 | 13.65/1 | 28.49 |
| 8 | zinc salt of synthetic acids[6] | 0.41 /0.0005 | U.A. | 5 /0.0537 | 25 /0.2775 | 1 | 140 | 160 (11) | 2.41/0.0159 | 0.12 /0.0011 | 0.34 /0.0017 | 20.08/1 | 29.61 |
| 9 | zinc tallate[7] | 0.409 /0.0005 | U.A. | 5 /0.0537 | 25 /0.2775 | 1 | 140 | 160 (11) | 3.87/0.0256 | 0.23 /0.0021 | 0.31 /0.0015 | 16.83/1 | 47.67 |
| 10 | zinc neodecanoate[8] | 0.2043 /0.0005 | U.A. | 5 /0.0537 | 25 /0.2775 | 1 | 140 | 160 (11) | 1.38/0.0091 | 0.17 /0.0016 | 0.06 /0.0003 | 8.12/1 | 16.95 |
| 11 | zinc octoate[9] | 0.182 /0.0005 | 4.85 | 5 /0.0537 | 25 /0.2775 | 1 | 140 | 160 (11) | 2.65/0.0175 | 0.26 /0.0024 | 0.26 /0.0013 | 10.19/1 | 32.59 |
| 12 | zinc salt of synthetic acids[6] | 1.021 /0.0025 | U.A. | 5 /0.0537 | 25 /0.2775 | 1 | 140 | 110 (8) | 6.7 /0.0443 | 0.16 /0.0015 | 0.15 /0.0007 | 41.88/1 | 82.5 |
| 13 | zinc salicylate | 0.98 /0.0025 | 3.00 | 5 /0.0537 | 25 /0.2775 | 2 | 140 | 110 (8) | 0.5 /0.0033 | 0.76 /0.0071 | 0.20 /0.0010 | 0.66/1 | 6.15 |
| 14 | zinc pivalate | 1.34 /0.005 | 5.02 | 5 /0.0537 | 25 /0.2775 | 2 | 140 | 200 (14) | 7.05/0.0466 | 0.13 /0.0012 | 0.12 /0.0006 | 54.23/1 | 86.78 |
| 15 | zinc pivalate | 1.34 /0.005 | 5.02 | 5 /0.0537 | 25 /0.2775 | 4 | 140 | 200 (14) | 7.84/0.0519 | 0.15 /0.0014 | 0.06 /0.0003 | 52.27/1 | 96.65 |
| 16 | zinc benzoate | 0.77 /0.0025 | 4.17 | 5 /0.0537 | 25 /0.2775 | 2 | 140 | 140 (10) | 4.57/0.0302 | 0.22 /0.0021 | 0.26 /0.0013 | 20.77/1 | 56.24 |
| 17 | zinc benzoate | 0.77 /0.0025 | 4.17 | 5 /0.0537 | 25 /0.2775 | 1 | 140 | 140 (10) | 7.26/0.048 | 0.28 /0.0026 | 0.22 /0.0011 | 25.93/1 | 89.39 |
| 18 | zinc stearate | 1.581 /0.0025 | U.A. | 5 /0.0537 | 25 /0.2775 | 2 | 140 | 150 (11) | 5.31/0.0351 | 0.12 /0.0011 | 0.15 /0.0007 | 44.25/1 | 65.36 |
| 19 | zinc acrylate | 0.519 /0.0025 | 4.25 | 5 /0.0537 | 25 /0.2775 | 2 | 140 | 160 (11) | 6.72/0.0445 | 0.10 /0.0009 | 0.58 /0.0028 | 67.20/1 | 82.87 |
| 20 | zinc parachlorobenzoate | 0.950 /0.0025 | 4.03 | 5 /0.0537 | 25 /0.2775 | 2 | 140 | 160 (11) | 6.73/0.0445 | 0.55 /0.0051 | 0.15 /0.0007 | 12.24/1 | 82.87 |
| 21 | zinc phenoxide | 0.63 /0.0025 | 10.00 | 5 /0.0537 | 25 /0.2775 | 5 | 140 | 140 (10) | 1.8 /0.0119 | 0.13 /0.0012 | 0.12 /0.0006 | 13.85/1 | 22.16 |
| 22 | stannous octoate | 1.02 /0.0025 | 4.85 | 5 /0.0537 | 25 /0.2775 | 2 | 140 | 110 (8) | 2.2 /0.0145 | 0.39 /0.0036 | 0.27 /0.0013 | 5.64/1 | 27.11 |
| 23 | zinc oxyacetate | 0.66 /0.0025 | 4.74 | 5 /0.0537 | 25 /0.2775 | 1 | 140 | 110 (8) | 4.9 /0.0324 | 0.03 /0.0003 | 0.15 /0.0007 | 143 /1 | 60.34 |
| 24 | zinc oxyacetate | 0.66 /0.0025 | 4.74 | 5 /0.0537 | 25 /0.2775 | 4 | 140 | 110 (8) | 7.1 /0.0470 | 0.15 /0.0014 | 0.12 /0.0006 | 47 /1 | 87.52 |
| 25 | zinc oxyacetate | 0.66 /0.0025 | 4.74 | 5 /0.0537 | 25 /0.2775 | 4 | 140 | 120 (8) | 7.3 /0.0483 | 0.18 /0.0017 | 0.072 /0.0004 | 41 /1 | 89.94 |
| 26 | zinc oxyacetate | 0.66 /0.0025 | 4.74 | 5 /0.0537 | 25 /0.2775 | 6 | 140 | 120 (8) | 7.7 /0.0509 | 0.28 /0.0026 | 0.14 /0.0007 | 28 /1 | 94.79 |
| 27 | zinc acetate | 0.46 /0.0025 | 4.74 | 5 /0.0537 | 25 /0.2775 | 1 | 140 | 160 (11) | 6.04/0.04 | 0.02 /0.0002 | 0.1 /0.0005 | 302 /1 | 74.49 |
| 28 | zinc acetate | 0.46 /0.0025 | 4.74 | 5 /0.0537 | 25 /0.2775 | 4 | 140 | 170 (12) | 7.1 /0.047 | 0.024/0.0002 | 0.1 /0.0005 | 296 /1 | 87.52 |
| 29 | zinc acetate | 0.46 /0.0025 | 4.74 | 5 /0.0537 | 25 /0.2775 | 4 | 140 | 140 (10) | 7.5 /0.0496 | 0.02 /0.0002 | 0.03 /0.0001 | 375 /1 | 92.36 |
| 30 | zinc acetate | 0.46 /0.0025 | 4.74 | 5 /0.0537 | 25 /0.2775 | 6 | 140 | 125 (9) | 8.1 92.36 | 0.02 /0.0002 | 0.06 /0.0003 | 405 /1 | 99.81 |
| 31 | zinc acetate dihydrate | 0.55 /0.0025 | 4.74 | 5 /0.0537 | 25 /0.2775 | 1 | 140 | 140 (10) | 6.1 /0.0404 | 0.24 /0.0022 | 0.18 /0.0009 | 25 /1 | 75.23 |
| 32 | zinc acetate dihydrate | 0.55 /0.0025 | 4.74 | 5 /0.0537 | 25 /0.2775 | 4 | 140 | 160 (11) | 7.0 /0.0463 | 0.27 /0.0025 | 0.15 /0.0007 | 26 /1 | 86.22 |
| 33 | zinc acetate dihydrate | 0.55 /0.0025 | 4.74 | 5 /0.0537 | 25 /0.2775 | 4 | 140 | 200 (14) | 7.3 /0.0483 | 0.33 /0.0031 | 0.03 /0.0001 | 22 /1 | 89.94 |
| 34 | zinc acetate dihydrate | 0.55 /0.0025 | 4.74 | 5 /0.0537 | 25 /0.2775 | 6 | 140 | 200 (14) | 7.5 /0.0496 | 0.24 /0.0022 | 0.06 0.0003 | 31 /1 | 92.36 |
| 35 | zinc chloride | 0.34 /0.0025 | N.A. | 5 /0.0537 | 25 /0.2775 | 1 | 140 | 150 (11) | 0.58 /0.0038 | 1.14 /0.0106 | 0.21 /0.0010 | 0.5 /1 | 7.08 |
| 36 | zinc chloride | 0.34 /0.0025 | N.A. | 5 /0.0537 | 25 /0.2775 | 4 | 140 | 160 (11) | 1.86/0.0123 | 1.47 /0.0137 | 0.03 /0.0001 | 1.3 /1 | 22.91 |
| 37 | zinc chloride | 0.34 /0.0025 | N.A. | 5 /0.0537 | 25 /0.2775 | 4 | 140 | 200 (14) | 2.76/0.0183 | 1.00 /0.0093 | 0.06 /0.0003 | 2.7 /1 | 17.32 |
| 38 | zinc chloride | 0.34 /0.0025 | N.A. | 5 /0.0537 | 25 /0.2775 | 6 | 140 | 200 (14) | 3.12/0.0206 | 0.6 /0.0056 | 0.06 /0.0003 | 5.2 /1 | 34.08 |
| 39 | zinc propionate | 0.53 /0.0025 | 4.88 | 5 /0.0537 | 25 /0.2775 | 1 | 140 | 80 (6) | 6.71/0.0444 | 0.12 /0.0011 | 0.12 /0.0006 | 56 /1 | 38.36 |
| 40 | zinc propionate | 0.55 /0.0025 | 4.88 | 5 /0.0537 | 25 /0.2775 | 4 | 140 | 140 (10) | 7.59/0.0502 | 0.12 /0.0011 | 0.07 /0.0003 | 61 /1 | 82.68 |
| 41 | zinc propionate | 0.53 /0.0025 | 4.88 | 5 /0.0537 | 25 /0.2775 | 4 | 140 | 150 (11) | 7.88/0.0521 | 0.12 /0.0011 | 0.06 /0.0003 | 66 /1 | 97.02 |
| 42 | zinc propionate | 0.53 /0.0025 | 4.88 | 5 /0.0537 | 25 /0.2775 | 6 | 140 | 150 (11) | 8 /0.0529 | 0.12 /0.0011 | 0.006 /0.0000 | 67 /1 | 98.51 |
| 43 | stannous chloride | 0.474 /0.0025 | N.A. | 5 /0.0537 | 25 /0.2775 | 1 | 140 | 70 (5) | 0.57/0.0038 | 0.51 /0.0048 | 0.018 /0.0001 | 1.1 /1 | 7.08 |

TABLE I-continued

| EXAMPLE OR EXPT. NO. | CATALYST TYPE | CATALYST g/mole | pKa[12] OF ORGANIC COMPOUND | ANILINE g/mole | DIMETHYL CARBONATE g/mole | REACTION TIME Hrs. | REACTION TEMP. °C. | CONDITIONS PRESS.[14] psi(kg/cm²) | REACTION PRODUCTS MPC[1] g/mole | NMA[2] g/mole | DPU[3] g/mole | WEIGHT RATIO MPC/NMA | % CONVERSION OF ANILINE TO MPC[10] |
|---|---|---|---|---|---|---|---|---|---|---|---|---|---|
| 44 | stannous chloride | 0.474/0.0025 | N.A. | 5/0.0537 | 25/0.2775 | 2 | 140 | 90 (6) | 3.43/0.0227 | 0.93/0.0087 | 0.066/0.0003 | 3.7/1 | 42.27 |
| 45 | stannous chloride | 0.474/0.0025 | N.A. | 5/0.0537 | 25/0.2775 | 4 | 140 | 100 (7) | 4.94/0.0327 | 0.72/0.0067 | 0.072/0.0004 | 6.9/1 | 60.89 |
| 46 | stannous chloride | 0.474/0.0025 | N.A. | 5/0.0537 | 25/0.2775 | 6 | 140 | 190 (13) | 2.94/0.0194 | 1.02/0.0095 | 0.072/0.0004 | 2.9/1 | 36.13 |
| E | antimony trichloride | 0.57/0.0025 | N.A.[13] | 5/0.0537 | 25/0.2775 | 1 | 140 | 80 (6) | 0.69/0.0046 | 0.45/0.0042 | 0.21/0.0010 | 1.5/1 | 8.57 |
| F | antimony trichloride | 0.57/0.0025 | N.A. | 5/0.0537 | 25/0.2775 | 2 | 140 | 120 (8) | 1.25/0.0083 | 0.26/0.0024 | 0.27/0.0013 | 4.8/1 | 15.46 |
| G | antimony trichloride | 0.57/0.0025 | N.A. | 5/0.0537 | 25/0.2775 | 4 | 140 | 150 (11) | 1.52/0.0101 | 1.29/0.0120 | 0.18/0.0009 | 1.2/1 | 18.81 |
| H | antimony trichloride | 0.57/0.0025 | N.A. | 5/0.0537 | 25/0.2775 | 6 | 140 | 190 (13) | 1.93/0.0128 | 1.32/0.0123 | 0.18/0.0009 | 1.5/1 | 23.84 |
| 47 | zinc acetate | 0.0917/0.0005 | 4.74 | 5/0.0537 | 25/0.2775 | 1 | 140 | 120 (8) | 3.2/0.0212 | 0.24/0.0022 | 0.15/0.0007 | 13/1 | 39.48 |
| 48 | zinc acetate | 0.0917/0.0005 | 4.74 | 5/0.0537 | 25/0.2775 | 2 | 140 | 120 (8) | 5.8/0.0384 | 0.36/0.0034 | 0.18/0.0009 | 16/1 | 71.51 |
| 49 | zinc acetate | 0.0917/0.0005 | 4.74 | 5/0.0537 | 25/0.2775 | 4 | 140 | 120 (8) | 6.4/0.0423 | 0.4/0.0037 | 0.15/0.0007 | 16/1 | 78.77 |
| 50 | zinc acetate | 0.0917/0.0005 | 4.74 | 5/0.0537 | 25/0.2775 | 6 | 140 | 120 (8) | 7.2/0.0476 | 0.4/0.0037 | 0.06/0.0003 | 18/1 | 88.64 |
| 51 | zinc propionate | 0.106/0.0005 | 4.88 | 5/0.0537 | 25/0.2775 | 1 | 140 | 40 (3) | 0.47/0.0031 | 0.07/0.0007 | 0/0 | 6.7/1 | 5.77 |
| 52 | zinc propionate | 0.106/0.0005 | 4.88 | 5/0.0537 | 25/0.2775 | 2.5 | 140 | 60 (4) | 2.79/0.0185 | 0.11/0.0010 | 0.28/0.0014 | 25/1 | 34.45 |
| 53 | zinc propionate | 0.106/0.0005 | 4.88 | 5/0.0537 | 25/0.2775 | 4 | 140 | 110 (8) | 4.47/0.0296 | 0.10/0.0009 | 0.45/0.0022 | 45/1 | 55.12 |
| 54 | zinc propionate | 0.016/0.0005 | 4.88 | 5/0.0537 | 25/0.2775 | 6 | 140 | 105 (7) | 6.62/0.0438 | 0.03/0.0003 | 0.10/0.0005 | 221/1 | 81.56 |
| 55 | zinc naphthenate | 0.41/0.0005 | U.A. | 5/0.0537 | 25/0.2775 | 1 | 140 | 140 (10) | 3./0.0198 | 0.18/0.0017 | 0.15/0.0007 | 17/1 | 36.87 |
| 56 | zinc naphthenate | 0.41/0.0005 | U.A. | 5/0.0537 | 25/0.2775 | 2 | 140 | 140 (10) | 5.15/0.0341 | 0.21/0.0020 | 1.23/0.0061 | 25/1 | 63.5 |
| 57 | zinc naphthenate | 0.41/0.0005 | U.A. | 5/0.0537 | 25/0.2775 | 4 | 140 | 140 (10) | 6.59/0.0436 | 0.54/0.0050 | 0.15/0.0007 | 12/1 | 81.19 |
| 58 | zinc naphthenate | 0.41/0.0005 | U.A. | 5/0.0537 | 25/0.2775 | 6 | 140 | 140 (10) | 6.99/0.0462 | 0.30/0.0028 | 0.06/0.0003 | 23/1 | 86.03 |
| 59 | zinc acetate | 1.03/0.0056 | 4.74 | 18.6/0.2 | 18/0.2 | 25.2 | 80 | 0 (0) | 0.6/0.004 | 0.2/0.0019 | 0/0 | 3/1 | 2.0 |
| I | uranium trioxide | 1.6/0.0056 | N.A. | 18.6/0.2 | 18/0.2 | 25.2 | 80 | 0 (0) | 0/0 | 0.10 | 0/0 | — | — |
| J | uranium trioxide | 1.6/0.0056 | N.A. | 18.6/0.2 | 18/0.2 | 25.2 | 80 | 0 (0) | 0.1/0.0007 | 0/0 | 0/0 | — | 0.35 |
| K | uranium trioxide | 1.6/0.0056 | N.A. | 18.6/0.2 | 18/0.2 | 48 | 80 | 0 (0) | 0.22/0.0015 | 0.4/0.0037 | 0.12/0.0006 | .55/1 | 0.75 |
| 60 | zinc octoate[9] | 1.83/0.0056 | 4.85 | 18.6/0.2 | 18/0.2 | 24.8 | 80 | 0 (0) | 6.7/0.0443 | 0.4/0.0037 | 0.2/0.001 | 17/1 | 22.15 |
| L | uranium dioxide | 1.51/0.0056 | N.A. | 18.6/0.2 | 18/0.2 | 24.8 | 80 | 0 (0) | 0/0 | 0/0 | 0/0 | — | — |
| 61 | zinc acetate | 1.61/0.0088 | 4.74 | 18.6/0.2 | 18/0.2 | 21 | 80 | 0 (0) | 0.5/0.0033 | 0/0 | 0/0 | — | 1.65 |
| M | antimony trichloride | 1.50/0.0088 | N.A. | 18.6/0.2 | 18/0.2 | 21 | 80 | 0 (0) | 4.1/0.0271 | 0.7/0.0065 | 0.6/0.003 | 5.9/1 | 13.55 |
| N | UO₂(NO₃)₂ . 6H₂O | 1.5/0.0030 | N.A. | 18.6/0.2 | 18/0.2 | 23.5 | 80 | 0 (0). | 2.6/0.0172 | 0.6/0.0056 | 0.13/0.0006 | 4.3/1 | 8.6 |
| 62 | zinc octoate[9] | 2.034/0.0056 | 4.85 | 5/0.0537 | 25/0.2775 | 2 | 200 | 400 (28) | 16.36/0.1082 | 2.49/0.0232 | 1.17/0.0058 | 6.6/1 | 54.1 |
| 63 | stannous octoate | 2.45/0.0056 | 4.85 | 5/0.0537 | 25/0.2775 | 2 | 200 | 550 (39) | 8.45/0.0559 | 4.34/0.0405 | 0.78/0.0039 | 1.9/1 | 27.95 |
| O | uranium trioxide | 1.60/0.0056 | N.A. | 5/0.0537 | 25/0.2775 | 2 | 200 | 700 (49) | 4.46/0.0295 | 6.37/0.0594 | 0.67/0.0033 | 0.7/1 | 14.75 |
| P | uranium dioxide | 1.51/0.0056 | N.A. | 5/0.0537 | 25/0.2775 | 2 | 200 | 650 (46) | 4.54/0.0300 | 6.36/0.0594 | 0.64/0.0032 | 0.7/1 | 15.0 |
| 64 | zinc formate | 0.48/0.0025 | 3.77 | 5/0.0537 | 25/0.2775 | 2 | 200 | 450 (32) | 2.9/0.02 | 2.9/0.027 | 0.09/0.0004 | 1/1 | 37.24 |
| 65 | zinc chloroacetate | 0.636/0.0025 | 2.85 | 5/0.0537 | 25/0.2775 | 2 | 200 | 280 (20) | 2.31/0.0153 | 0.30/0.0028 | 0/0 | 7.7/1 | 28.46 |
| 66 | zinc trifluoroacetate | 0.734/0.0025 | 0.23 | 5/0.0537 | 25/0.2775 | 2 | 200 | 390 (27) | 2.88/0.019 | 0.84/0.0078 | 0.06/0.0003 | 3.43/1 | 35.48 |
| 67 | zinc octoate[9] | 0.185/0.0025 | 4.83 | 5/0.0537 | 25/0.2775 | 0.25 | 200 | 290 (20) | 2.02/0.0134 | 0.41/0.0038 | 0.35/0.0016 | 85 | 24.88 |
| 68 | zinc octoate[9] | 0.185/0.0025 | 4.85 | 5/0.0537 | 25/0.2775 | 0.50 | 200 | 290 (20) | 4.32/0.029 | 0.67/0.0063 | 0.35/0.0016 | 6.45/1 | 53.22 |
| 69 | zinc octoate[9] | 0.185/0.0025 | 4.85 | 5/0.0537 | 25/0.2775 | 1 | 200 | 300 (21) | 6.51/0.043 | 0.70/0.0065 | 0.07/0.0003 | 9.3/1 | 80.19 |
| 70 | zinc octoate[9] | 0.185/0.0025 | 4.85 | 5/0.0537 | 25/0.2775 | 2 | 200 | 300 (21) | 6.66/0.044 | 0.54/0.005 | 0.05/0.0002 | 12.33/1 | 82.04 |
| 71 | zinc thiodipropionic acid | 0.604/0.0025 | U.A. | 5/0.0537 | 25/0.2775 | 1 | 200 | 210 (15) | 1.77/0.12 | 0.78/0.0073 | 0.20/0.0009 | 2.27/1 | 21.80 |
| 72 | stannous chloride | 0.474/0.0025 | N.A. | 5/0.0537 | 25/0.2775 | 1 | 200 | 210 (15) | 7.41/0.049 | 0.33/0.003 | 0.13/0.0006 | 22.45/1 | 91.28 |

TABLE I-continued

| EXAMPLE OR EXPT. NO. | CATALYST | | pKa[12] OF ORGANIC COMPOUND | ANILINE g/mole | DIMETHYL CARBONATE g/mole | REACTION | | CONDITIONS PRESS.[14] psi(kg/cm²) | REACTION PRODUCTS | | | WEIGHT RATIO MPC/NMA | % CONVERSION OF ANILINE TO MPC[10] |
|---|---|---|---|---|---|---|---|---|---|---|---|---|---|
| | TYPE | g/mole | | | | TIME Hrs. | TEMP. °C. | | MPC[1] g/mole | NMA[2] g/mole | DPU[3] g/mole | | |
| 73 | zinc acetate | 0.46 /0.0025 | 4.74 | 5 /0.0537 | 25 /0.2775 | 1 | 200 | 280 (20) | 7.2 /0.048 | 0.21 /0.003 | 0.06 /0.0003 | 34.3 /1 | 88.7 |

[1]MPC is methyl phenyl carbamate.
[2]NMA is N-methyl aniline.
[3]DPU is diphenyl urea.
[4]zinc salt of a highly refined naphthenic acid containing 8% zinc and commercially available from Mooney Chemical, Inc. as a Nap-All drier.
[5]zinc salt of a blend of synthetic domestic acid containing 10% zinc and commercially available from Mooney Chemical, Inc. as a Nap-All drier.
[6]zinc salt of a blend of synthetic domestic acid containing 8% or 16% zinc and commercially available from Mooney Chemicals, Inc. as a Chem-All drier.
[7]zinc salt of extra-pale tall oil acids containing 8% zinc and commercially available from Mooney Chemicals, Inc. as a Lin-All drier.
[8]zinc salt of a domestic, synthetic neodecanoic acid containing 16% zinc and commercially available from Mooney Chemicals, Inc. as a Ten-Cem drier.
[9]a zinc salt of 2-ethylhexanoic acid containing 18% zinc and commercially available from Mooney Chemicals, Inc. as a Hex-Cem drier.
[10]Calculated by dividing moles of MPC produced by moles of aniline employed and multiplying by 100.
[11]U.A. means unavailable by the applicant (i.e. is not in the literature reviewed).
[12]pKa is the pKa value of the compound from which the catalyst is derived; e.g. for zinc acetate it is the value for acetic acid.
[13]N.A. means not applicable (i.e. not a derivative of an organic acid).
[14]Pressure indicated is gauge pressure.

EXAMPLES 74-98 AND COMPARATIVE EXPERIMENTS Q-U

Equimolar amounts of aniline and ethylene carbonate were mixed together. Then 10 gram quantities (5.14 g, 0.0552 mole aniline; 4.86 g, 0.0552 mole ethylene carbonate) of this mixture were weighed into each of a series of 4 dram (15 cc) glass vials. Various catalysts, one per vial, were then weighed into the vials and mixed. The vials were then placed, unsealed, in a metal block of a "Temp Blok" module heater with thermostatic control to hold any desired temperature and the mixture heated for the desired time. Small aliquots could be removed periodically and analyzed for the degree of carbamate formation, if any.

The various catalysts and quantity of catalyst, reaction conditions and results are given in Table II.

ture was 96° C. On cooling, no precipitate of diphenyl urea was observed and 203 g of solution remaining contained the following:
0.24 g (0.0012 mole) of diphenyl urea
38.0 g (0.2514 mole) of methyl phenyl carbamate
12.18 g (0.1308 mole) of aniline
1.0 g (0.0093 mole) of N-methyl aniline.

B. Comparative experiment employing antimony trichloride as the catalyst

In like manner as A above, 180 g (2 moles) dimethyl carbonate, 37.2 g (0.4 mole) aniline and 11.4 g (0.05 mole) antimony trichloride were employed. The antimony trichloride formed a dense white suspension of complex with aniline. The reaction temperature was 98° C. On cooling, solid diphenyl urea separated. Upon filtering, 11.3 g of solid diphenyl urea was obtained.

TABLE II

| EXAMPLE OR COMP. EXPT. NO. | CATALYST TYPE | g/mole | $pKa^3$ OF ORGANIC COMPOUND | REACTION TIME Hrs. | CONDITIONS TEMP. °C. | REACTION PRODUCTS HENPC[1] g/mole | NHA[2] g/mole | WEIGHT RATIO HENPC/NHEA | % CONVERSION OF ANILINE TO HENPC[5] |
|---|---|---|---|---|---|---|---|---|---|
| 74 | zinc acetate | 0.2 /.0011 | 4.74 | 16 | 108 | 4.67/0.0258 | 0.84 /0.0061 | 5.56/1 | 46.74 |
| 75 | zinc acetate | 0.2 /.0012 | 4.74 | 48 | 108 | 3.99/0.0220 | 1.24 /0.0090 | 3.22/1 | 39.86 |
| Q | ferric chloride | 0.2 /.0011 | N.A.[4] | 40 | 108 | 2.79/0.0154 | 1.98 /0.0144 | 1.41/1 | 27.9 |
| 76 | zinc salicylate | 0.2 /.0025 | 3.00 | 36 | 108 | 2.26/0.0125 | 1.0 /0.0073 | 2.26/1 | 22.64 |
| 77 | zinc stearate | 0.2 /.0003 | U.A.[6] | 36 | 108 | 3.07/0.0169 | 1.47 /0.0107 | 2.09/1 | 30.62 |
| 78 | zinc acrylate | 0.2 /.0015 | 4.25 | 36 | 108 | 2.33/0.0129 | 0.88 /0.0064 | 2.65/1 | 23.37 |
| 79 | zinc di(2-aminoethyl sulfide) | 0.2 /.00092 | N.A.[4] | 36 | 108 | 4.13/0.0228 | 1.05 /0.0077 | 3.93/1 | 41.3 |
| 80 | zinc trifluoracetate | 0.2 /.0011 | 0.23 | 36 | 108 | 4.13/0.0228 | 0.97/0.0071 | 4.26/1 | 41.3 |
| 81 | stannous chloride | 0.1 /.00053 | N.A.[4] | 40 | 90 | 3.56/0.0196 | 1.11 /0.0081 | 3.21/1 | 35.51 |
| R | stannous oxalate | 0.1 /.00048 | 1.23 | 40 | 90 | 0.18/0.001 | 1.21 /0.0088 | 0.15/1 | 1.81 |
| 82 | zinc acetate | 0.1 /.00055 | 4.74 | 40 | 90 | 3.36/0.0185 | 0.81 /0.0059 | 4.15/1 | 33.51 |
| 83 | zinc acetate | 0.1 /.00055 | 4.74 | 40 | 90 | 4.97/0.0274 | 1.01 /0.0074 | 4.92/1 | 49.64 |
| 84 | zinc di(2-aminoethyl sulfide) | 0.1 /.00046 | N.A.[4] | 40 | 90 | 3.51/0.0194 | 0.51 /0.0037 | 6.88/1 | 35.14 |
| 85 | zinc di(2-aminoethyl sulfide) | 0.1 /.00046 | N.A.[4] | 40 | 90 | 5.05/0.0279 | 1.01 /0.0074 | 5.00/1 | 50.54 |
| 86 | zinc chloride | 0.18/.0013 | N.A.[4] | 44 | 90 | 3.09/0.0171 | 1.10 /0.0080 | 2.81/1 | 30.98 |
| 87 | zinc acetylacetonate | 0.05/.0003 | 9.00 | 44 | 90 | 3.54/0.0195 | 1.02 /0.0074 | 3.47/1 | 35.33 |
| 88 | stannous laurate | 0.2 /.0004 | N.A.[4] | 44 | 90 | 0.10/0.0006 | 1.15 /0.0084 | 0.09/1 | 1.09 |
| S | ferric chloride | 0.02/.00011 | N.A.[4] | 44 | 90 | 0.66/0.0036 | 1.21 /0.0088 | 0.55/1 | 6.52 |
| 89 | stannous octoate | 0.4 /.0009 | 4.9 | 72 | 90 | 4.27/0.0236 | 0.73 /0.0053 | 5.85/1 | 42.75 |
| T | aluminum trichloride | 0.06/.00045 | N.A.[4] | 72 | 90 | 1.58/0.0087 | 2.98 /0.0217 | 0.53/1 | 15.76 |
| 90 | zinc acetate | 0.02/.00011 | 4.74 | 72 | 100 | 2.52/0.0139 | 1.66 /0.0121 | 1.52/1 | 25.18 |
| 91 | zinc acetate | 0.5 /.0027 | 4.74 | 72 | 100 | 3.95/0.0218 | 0.72 /0.0052 | 5.49/1 | 39.49 |
| 92 | zinc acetate | 0.1 /.00055 | 4.74 | 24 | 90 | 3.06/0.0169 | 0.6 /0.0047 | 4.78/1 | 30.62 |
| 93 | zinc acetate | 0.3 /.0016 | 4.74 | 24 | 90 | 3.74/0.0206 | 0.525/0.0038 | 7.12/1 | 37.32 |
| 94 | zinc acetate | 0.5 /.0027 | 4.74 | 24 | 90 | 3.96/0.0219 | 0.43 /0.0031 | 9.2/1 | 39.67 |
| 95 | zinc acetate | 1.0 /0.0055 | 4.74 | 24 | 90 | 4.08/0.0225 | 0.36/0.0026 | 11.33/1 | 40.76 |
| 96 | zinc trifluoroacetate | 0.2/0.0007 | 0.23 | 36 | 108 | 4.13/0.0228 | 1.11/0.0081 | 3.72/1 | 41.3 |
| 97 | zinc formate | 0.2 /0.001 | 3.75 | 36 | 108 | 4.46/0.0246 | 1.77/0.0129 | 2.52/1 | 44.57 |
| U | zinc oxalate | 0.2 /0.0001 | 1.23 | 36 | 108 | 0.19/0.001 | 3.47/0.0253 | 0.05/1 | 1.81 |
| 98 | zinc chloroacetate | 0.2 /0.0008 | 2.85 | 36 | 108 | 2.17/0.0120 | 3.48/0.0254 | 0.62/1 | 21.74 |

[1] HENPC is hydroxyethyl N-phenyl carbamate.
[2] NHEA is N-hydroxyethyl aniline.
[3] pKa is the pKa value of the compound from which the metal catalyst salt was derived; e.g. for zinc acetate, it is the value of acetic acid.
[4] N.A. means not applicable since the catalyst is a salt of a mineral acid or a compound other than carboxylate.
[5] calculated by dividing moles of HENPC produced by moles of aniline employed and multiplying by 100.
[6] U.A. means unavailable by the applicant (i.e. is not in the literature reviewed).

EXAMPLE 99

A. Present invention employing zinc acetate as the catalyst

To a 500 ml reaction vessel fitted with a means for heating and reflux azeotrope removal, was added 180 g (2 moles) of dimethyl carbonate, 37.2 g (0.4 mole) of aniline and 9.2 g (0.05 mole) of anhydrous zinc acetate. The zinc acetate was completely soluble in the reaction mixture. The reaction mixture was refluxed for 6 hours while slowly taking off an azeotropic mixture of dimethyl carbonate and methanol. The reaction tempera- The filtrate was analyzed and found to contain:
1.2 g (Total=12.5 g, 0.0618 mole) of diphenyl urea
10.37 g (0.0686 mole) of methyl phenyl carbamate
2.0 g (0.0187 mole) of N-methyl aniline
11.86 g (0.13 mole) of aniline.

EXAMPLES 100 TO 113

These examples were prepared in the same manner as those for Examples 1-63 except that different amines were employed. The reactants, reaction conditions and results are given in the following Table III.

TABLE III

| EXAMPLE NUMBER | CATALYST TYPE | CATALYST g/mole | pKa[6] OF ORGANIC COMPOUND | AMINE TYPE | AMINE g/mole | DIMETHYL CARBONATE g/mole | REACTION TIME Hrs. | REACTION TEMP. °C | CONDITIONS PRESS. psi (kg/cm²) | DICARBAMATE g/mole | % CONVERSION OF AMINE TO DICARBAMATE[5] |
|---|---|---|---|---|---|---|---|---|---|---|---|
| 100[1] | zinc acetate | 0.46/0.0025 | 4.74 | 2,6-diaminotoluene | 3.4/0.0279 | 25/0.2775 | 4 | 140 | 180 (13) | 1.61/.00678 | 24.4 |
| 101 | zinc acetate | 0.46/0.0025 | 4.74 | 2,6-diaminotoluene | 3.4/0.0279 | 25/0.2775 | 4 | 140 | 240 (17) | 2.37/.01 | 36.0 |
| 102 | zinc octoate (18% Zn)[2] | 1.82/0.005 | U.A.[4] | 2,6-diaminotoluene | 3.45/0.0283 | 25/0.2775 | 4 | 160 | 220 (15) | 2.54/.0107 | 37.8 |
| 103 | zinc octoate (18% Zn)[2] | 1.82/0.005 | U.A.[4] | 2,4-diaminotoluene | 3.4/0.0279 | 25/0.2775 | 4 | 140 | 240 (17) | 2.12/.0089 | 32.0 |
| 104 | zinc octoate (18% Zn)[2] | 1.82/0.005 | U.A.[4] | 2,4-diaminotoluene | 3.4/0.0279 | 25/0.2775 | 7 | 160 | 190 (13) | 4.9/.0206 | 74.0 |
| 105 | zinc octoate (18% Zn)[2] | 1.82/0.005 | 4.74 | 2,4-diaminotoluene | 3.45/0.0283 | 25/0.2775 | 4 | 160 | 220 (15) | 3.92/.0165 | 58.3 |
| 106[3] | zinc acetate | 0.46/0.0025 | 4.74 | 2,4-diaminotoluene | 3.4/0.0283 | 25/0.2775 | 4 | 140 | 140 (10) | 1.22/.005 | 18.3 |
| 107[7,8,9] | zinc propionate | 0.534/0.0025 | 4.88 | p-toluidine | 5.75/0.0537 | 32.8/0.2775 | 4 | 140 | 110 (8) | 6.42/.0387 | 72 |
| 108 | zinc octoate (18% Zn)[2] | 0.363/0.001 | 4.85 | 2,4-diaminotoluene | 3.05/0.025 | 22.5/0.25 | 3 | 200 | 300 (21) | 2.44/.01 | 40 |
| 109[7] | zinc acetate | 0.46/0.0025 | 4.74 | o-anisidine | 6.2/0.05 | 22.5/0.25 | 2 | 160 | 220 (15) | 5.6/0.031 | 62 |
| 110[7] | zinc acetate | 0.46/0.0025 | 4.74 | m-anisidine | 6.2/0.005 | 22.5/0.25 | 2 | 160 | 220 (15) | 6.6/0.037 | 74 |
| 111[7] | zinc acetate | 0.46/0.0025 | 4.74 | p-anisidine | 6.2/0.05 | 22.5/0.25 | 2 | 160 | 220 (15) | 8.0/0.044 | 88 |
| 112[7,8,9,10] | zinc octoate (18% Zn)[2] | 0.911/0.0025 | U.A.[4] | aniline | 5/0.0537 | 25/0.212 | 2 | 200 | 180 (13) | 4.8/0.027 | 54 |
| 113[11,12] | zinc propionate | 0.55/0.0258 | 4.88 | aniline | 4/0.043 | 23/0.1073 | 5 | 140 | 110 (8) | good yield | — |

[1]also contained 25 grams of dioxane as a reaction diluent.
[2]a zinc salt of 2-ethylhexanoic acid containing 18% zinc and commercially available from Mooney Chemicals, Inc., as a Hex-Cem drier.
[3]Also contained 25 grams dimethyl ether of ethylene glycol as a reaction diluent.
[4]U.A. means unavailable by the applicant (i.e. is not in the literature reviewed).
[5]Calculated by dividing moles of dicarbamate produced by moles of amine employed and multiplying by 100.
[6]pKa is the pKa value of the compound from which the metal catalyst salt was derived; e.g. for zinc acetate, it is the value of acetic acid.
[7]Product was a monocarbamate instead of a dicarbamate.
[8]Employed diethyl carbonate instead of dimethyl carbonate.
[9]The results were approximated using the calibration curve for methyl phenyl carbamate.
[10]The wt. ratio of ethyl phenyl carbamate to undesired N-ethyl aniline was 253 to 1.
[11]Employed diphenyl carbonate instead of dimethyl carbonate.
[12]Also employed 20 grams of acetonitrile as a reaction medium.

Zinc acetate was also found to be suitable for catalyzing the reaction between dimethyl carbonate and methylene dianiline, o-phenylenediamine, m-phenylenediamine, p-phenylenediamine, and an 80/20 mixture of 2,4-/2,6-diamino toluene.

Zinc naphthenate (80% Zn) was also found to be suitable for catalyzing the reaction between dimethyl carbonate and 2,6-diamino toluene and an 80/20 mixture of 2,4-/2,6-diamino toluene.

Zinc octoate (18% Zn) was found to not catalyze the reaction between dimethyl carbonate and 2,4,6-tribromoaniline.

I claim:

1. In a process for preparing carbamates from an organic carbonate and an aromatic amine in the presence of catalytic quantities of a Lewis acid catalyst; the improvement which comprises employing as the Lewis acid catalyst, a zinc or divalent tin halide, zinc or divalent tin salt of a monovalent organic compound which has a pKa value of at least 2.8, a zinc or divalent tin salt of trifluoroacetic acid or a mixture of such catalysts and which is soluble in the reaction mixture at the reaction conditions employed; with the proviso that when a zinc or divalent tin salt of trifluoroacetic acid is employed as the only catalyst, the organic carbonate is a cyclic organic carbonate.

2. The process of claim 1 wherein the compound has a pKa of from about 4 to about 10, the reaction temperature is from about 80° C. to about 300° C.

3. The process of claim 2 wherein the reaction temperature is from about 120° C. to about 250° C.

4. The process of claim 3 wherein the catalyst is a zinc salt and the temperature is from about 130° C. to about 200° C.

5. The process of claim 4 wherein the catalyst is selected from zinc naphthenate, zinc acetate, zinc propionate, zinc octoate or mixtures thereof.

6. The process of claim 1, 2, 3 or 4 wherein said catalyst is zinc carbonate, cobaltous acetylacetonate, or mixtures thereof.

7. The process of claim 1, 2, 3, 4 or 5 wherein said aromatic amine is aniline, 2,4-toluene diamine, 2,6-toluene diamine, methylene dianiline or mixtures thereof and said organic carbonate is dimethylcarbonate, diethylcarbonate, diphenylcarbonate, ethylene carbonate, propylene carbonate or mixtures thereof.

8. The process of claim 6 wherein said aromatic amine is aniline, 2,4-toluene diamine, 2,6-toluene diamine, methylene dianiline or mixtures thereof and said organic carbonate is dimethylcarbonate, diethylcarbonate, diphenylcarbonate, ethylene carbonate, propylene carbonate or mixtures thereof.

* * * * *

UNITED STATES PATENT AND TRADEMARK OFFICE
CERTIFICATE OF CORRECTION

PATENT NO. : 4,268,683
DATED : May 19, 1981
INVENTOR(S) : Arthur E. Gurgiolo

It is certified that error appears in the above-identified patent and that said Letters Patent are hereby corrected as shown below:

Under Abstract, 1st line change "cabonates" to --carbonates--.

Table 1, Example 30 under the heading $MPC^1$ g/mole change "8.1/92.36" to --8.1/0.0536--.

Table 1 Example 34 under the heading $DPU^3$ g/mole change "0.06,0.0003" to --0.06/0.0003--.

Table 1 Example 54 under the heading catalyst g/mole change "0.016/0.0005" to 0.106/0.0005--.

Table 1 Example I under the heading Reaction Products $NMA^2$ g/mole change "010" to --0/0--.

Table 1 Example 67 under the heading Weight Ratio MPC/NMA change "85" to --4.93/1--.

Table 1 Example 70 under the heading Catalyst g/mole change "0.185 0.0025" to --0.185/0.0025--.

Table 1 Example 73 under the heading Reaction Products $NMA^2$ g/mole change "0.21/0.003" to --0.21/0.002--.

In footnote number 12 change "v as " to --was--.

Table 2 Example 4 under the heading Catalyst g/mole change "0.2/0.0001" to --0.2/0.001--.

Table 3 Example $110^7$ under the heading amine g/mole change "6.2/0.005" to --6.2/0.05--.

Column 16, Claim 6 line 1 change "claim to --claims--.

UNITED STATES PATENT AND TRADEMARK OFFICE
CERTIFICATE OF CORRECTION

PATENT NO. : 4,268,683

DATED : May 19, 1981

INVENTOR(S) : Arthur E. Gurgiolo

It is certified that error appears in the above-identified patent and that said Letters Patent are hereby corrected as shown below:

Column 16, claim 7 line 1 change "claim" to --claims--.

Signed and Sealed this

Twenty-ninth Day of September 1981

[SEAL]

Attest:

Attesting Officer

GERALD J. MOSSINGHOFF

Commissioner of Patents and Trademarks